US006177427B1

(12) United States Patent
Clark et al.

(10) Patent No.: US 6,177,427 B1
(45) Date of Patent: Jan. 23, 2001

(54) TREATMENT OF GLAUCOMA AND OCULAR HYPERTENSION

(75) Inventors: Abbot F. Clark, Arlington; Raymond E. Conrow, Fort Worth, both of TX (US)

(73) Assignee: Alcon Laboratories, Inc., Fort Worth, TX (US)

(*) Notice: Under 35 U.S.C. 154(b), the term of this patent shall be extended for 0 days.

(21) Appl. No.: 09/346,424

(22) Filed: Jul. 1, 1999

Related U.S. Application Data

(63) Continuation of application No. 08/858,298, filed on May 19, 1997, now abandoned, which is a continuation of application No. 08/631,041, filed on Apr. 12, 1996, now abandoned, which is a continuation of application No. 08/268,086, filed on Jun. 28, 1994, now abandoned.

(51) Int. Cl.$^7$ ............ A61K 31/415; C07D 231/10; C07D 207/04; C07D 265/30
(52) U.S. Cl. ............ 514/239.2; 514/255; 514/383; 514/396; 514/406; 544/177; 544/396; 548/262.2; 548/373.1; 548/572
(58) Field of Search ............ 514/396, 397, 514/239.2, 255, 406, 383; 548/346.1, 314.7, 262.2, 572, 373.1; 544/177, 396

(56) References Cited

U.S. PATENT DOCUMENTS

| | | | | |
|---|---|---|---|---|
| 3,321,366 | * | 5/1967 | Mussell et al. | 167/33 |
| 3,657,445 | * | 4/1972 | Buchel et al. | 424/273 |
| 3,897,438 | * | 7/1975 | Draber et al. | 260/296 R |
| 5,234,634 | * | 8/1993 | Janoff et al. | 264/4.1 |

OTHER PUBLICATIONS

Loose et al., "Ketoconazole binds to glucocorticoid receptors and exhibits glucocrticoid antagonist activity in cultured cells." J. Clin. Invest., vol. 72, pp. 404–408, 1983.*

Lorenzetti, "Effects of corticosteroids on ocular dynamics in rabbits." J. Pharm. Exp. Ther., vol. 175(3), pp. 763–772, 1970.*

Zhan et al., "Steoid glaucoma: Corticosteroid–induced ocular hypertension in cats." Exp. Eye Res., vol. 54, pp. 211–218, 1992.*

Kass, et al., Corticosteroid–induced glaucoma, In Ritch, R., Shields, M.B., Krupin, T. (eds.), The Glaucomas, The C. V. Mosby Company, St. Louis, MO, pp. 1161–1168 (1989).

DeSantis, et al., Dexamethasone–induction of ocular hypertension in the primate, ARVO Abstracts. Invest. Ophthalmol. Vis. Sci. 31(Suppl.):99 (1990).

Knepper, et al., Intracular pressure and glycosaminoglycan distribution in the rabbit eye: effect of age and dexamethasone, Exp. Eye Res. 27:567–575 (1978).

Francois, et al., Ultrasonic and morphometric study of corticosteroid glaucoma in rabbits, Ophthalmic Res. 16:168–178 (1984).

Lorenzetti, O. J., Effects of corticosteroids on ocular dynamics in rabbits, J. Pharmacol. Exp. Therap. 175:763–772 (1970).

Zhan, et al., Steroid glaucoma: corticosteroid–induced ocular hypertension in cats, Exp. Eye Res. 53:211–218 (1992).

Rozsival, et al., Aqueous humour and plasma cortisol levels in glaucoma and cataract patients, Current Eye Research 1:391–396 (1981).

Ray, et al., Plasma cortisol in glaucoma, Ann. Ophthalmol. 9: 1151–1154 (1977).

Schwartz, Increased plasma free cortisol in ocular hypertension and open angle glaucoma, Arch. Ophthalmol. 105: 1060–1065 (1987).

Wilson, et al., Dexamethasone induced ultrastructural changes in cultured human trabecular meshwork cells, Cur. Eye Res. 12:783–793 (1993).

Clark, et al., Glucocorticoid–induced formation of cross–linked actin networks in cultured human trabecular meshwork cells, Invest. Ophthalmol. Vis. Sci. 35:281–294 (1994).

Loose, et la., Ketoconazole Binds to Glucocorticoid Receptors and Exhibits Glucocorticoid Antagonist Activity in Cultured Cells, J. Clin. Invest. 72:404–408 (1983).

* cited by examiner

*Primary Examiner*—Barbara Badio
(74) *Attorney, Agent, or Firm*—Sally Yeager

(57) ABSTRACT

Compositions of non-steroidal glucocorticoid antagonists for treating glaucoma or ocular hypertension and methods for their use are disclosed.

3 Claims, No Drawings

TREATMENT OF GLAUCOMA AND OCULAR HYPERTENSION

This application is a continuation of U.S. Ser. No. 08/858,298, filed on May 19, 1997, now abandoned, which is a continuation of U.S. Ser. No. 08/631,041, filed Apr. 12, 1996, now abandoned, which is a continuation of U.S. Ser. No. 08/268,086, filed on Jun. 28, 1994, now abandoned.

This invention is directed to the use of non-steroidal glucocorticoid antagonists for treating glaucoma and ocular hypertension.

BACKGROUND OF THE INVENTION

Current glaucoma therapy involves treating an important risk factor for the disease, that is, elevated intraocular pressure (IOP). For example, beta-blockers and carbonic anhydrase inhibitors lower IOP by decreasing aqueous humor production. It would be advantageous to control IOP without decreasing aqueous humor production as the aqueous humor is the fluid that nourishes the anterior parts of the eye that are devoid of blood vessels, such as, the cornea and the lens.

SUMMARY OF THE INVENTION

Non-steroidal glucocorticoid antagonists (NSGAs) and their pharmaceutical formulations are useful for treating glaucoma and ocular hypertension. The invention is also directed to methods for controlling glaucoma and ocular hypertension using NSGAs, some of which are novel.

DESCRIPTION OF THE PREFERRED EMBODIMENTS

Glaucomatous damage to vision is usually due to elevated IOP in a pressure sensitive eye. In glaucoma the trabecular meshwork (TM) of the eye is damaged causing increased aqueous humor outflow resistance resulting in elevated IOP. Glucocorticoids have been associated with the development of ocular hypertension and primary open angle glaucoma (Kass, et al., *Corticosteroid-induced glaucoma,* In Ritch, R., Shields, M. B., Krupin, T. (eds.), The Glaucomas, The C. V. Mosby Company, St. Louis, Mo., pp. 1161–1168 (1989); DeSantis, et al., *Dexamethasone-induction of ocular hypertension in the primate,* ARVO Abstracts. Invest. Ophthalmol. Vis. Sci. 31 (Suppl.): 99 (1990); Knepper, et al., *Intraocular pressure and glycosaminoglycan distribution in the rabbit eye: effect of age and dexamethasone,* Exp. Eye Res. 27: 567–575 (1978); Francois, et al., *Ultrastructural and morphometric study of corticosteroid glaucoma in rabbits,* Ophthalmic Res. 16: 168–178 (1984); Lorenzetti, O. J., *Effects of corticosteroids on ocular dynamics in rabbits,* J. Pharmacol. Exp. Therap. 175: 763–772 (1970); and Zhan, et al., *Steroid glaucoma: corticosteroid-induced ocular hypertension in cats,* Exp. Eye Res. 54: 211–218 (1992)). Glaucoma patients have also been reported to have higher levels of the endogenous glucocorticoid, cortisol (Rozsival, et al., *Aqueous humour and plasma cortisol levels in glaucoma and cataract patients,* Current Eye Research 1: 391–396 (1981); Ray, et al., *Plasma cortisol in glaucoma,* Ann. Ophthalmol. 9: 1151–1154 (1977); and Schwartz, *Increased plasma free cortisol in ocular hypertension and open angle glaucoma,* Arch. Ophthalmol. 105: 1060–1065 (1987)).

It is known that trabecular meshwork cells have glucocorticoid receptors and that glucocorticoid binding with these receptors causes a change in trabecular as meshwork cell gene expression. Known manifestations of this change include a reorganization of the cytoskeleton (Wilson, et al., *Dexamethasone induced ultrastructural changes in cultured human trabecular meshwork cells,* Cur. Eye Res. 12: 783–793 (1993) and Clark, et al., *Glucocorticoid-induced formation of cross-linked actions networks in cultured human trabecular meshwork cells,* Invest. Ophthalmol. Vis. Sci. 35: 281–294 (1994)) and increased deposition of the extracellular matrix material in trabecular meshwork cells. As a result, the trabecular meshwork becomes "clogged" and unable to perform one of its most critical functions, that is, serving as a gateway for aqueous humor flow from the anterior chamber of the eye. When the aqueous humor flow out of the eye via the trabecular meshwork is diminished, the intraocular pressure of the eye rises. If this state of elevated intraocular pressure is maintained or frequently occurs, the optic nerve head can be damaged resulting in the loss of visual field. Loss of visual field is the hallmark symptom associated with glaucoma.

Endogenous glucocorticoids may be responsible for producing the changes in the trabecular meshwork that lead to ocular hypertension and glaucoma. It is believed that non-steroidal glucocorticoid antagonists bind to the glucocorticoid receptor in trabecular meshwork cells, and thereby prevent binding of endogenous glucocorticoids to the glucocorticoid receptor. They may also displace endogenous glucocorticoids which are bound to glucocorticoid receptors. Use of the compounds of the present invention is advantageous over existing therapies in that the compounds function at the disease site, that is, at the trabecular meshwork cell level, rather than indirectly addressing elevated intraocular pressure by suppressing aqueous humor formation.

Ketoconazole and clotrimazole are known glucocorticoid antagonists. (Loose, et al., *Ketoconazole Binds to Glucocorticoid Receptors and Exhibits Glucocorticoid Antagonist Activity in Cultured Cells,* J. Clin. Invest. 72: 404–408 (1983)). They are not known to be useful in treating or controlling glaucoma.

Non-steroidal glucocorticoid antagonists which are particularly useful in treating glaucoma or ocular hypertension have the following structure:

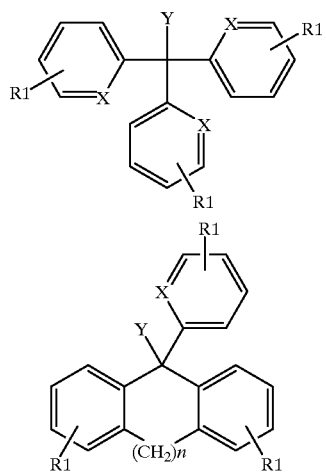

WHEREIN:
n=0,1,2;
X=CH or N;
R1=H, F, Cl, Br, R2, OR2, N(R2)$_2$, COOH, CONH$_2$, CONHR2, CON(R2)$_2$, CH$_2$N(CH$_2$CH$_2$)O;

R2=$C_1$–$C_6$ alkyl;
Y=N-imidazolyl, N-pyrrolidinyl, N-(2-hydroxymethyl) pyrrolidinyl, N-triazolyl, N-pyrazolyl each optionally substituted with $CH_3$, SH or S—C(4—Cl—$C_6H_4)_3$; OH, $O(CH_2)_2N(CH_2CH_2)_2O$, $O(CH_2)_2N(CH_2CH_2)_2N(CH_2)_2OH$;
and all pharmaceutically acceptable salts and esters.
Most preferred compounds include the following specific compounds:
(1)
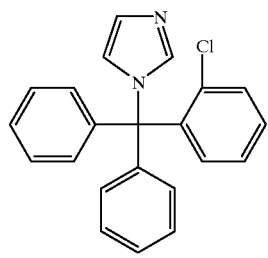
(2)
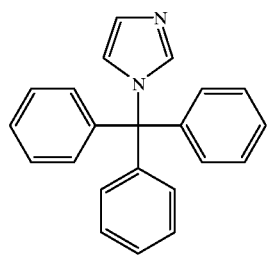
(3)
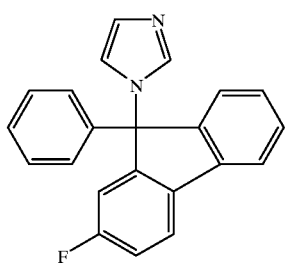
(4)
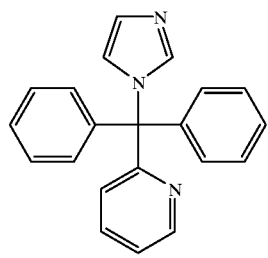
-continued
(5)
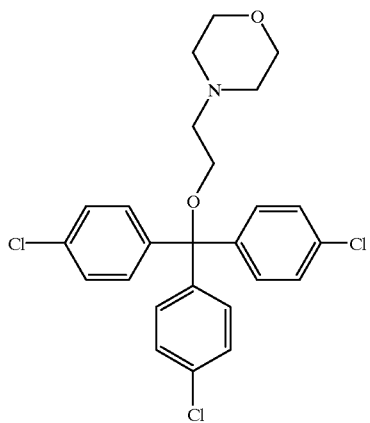
(6)
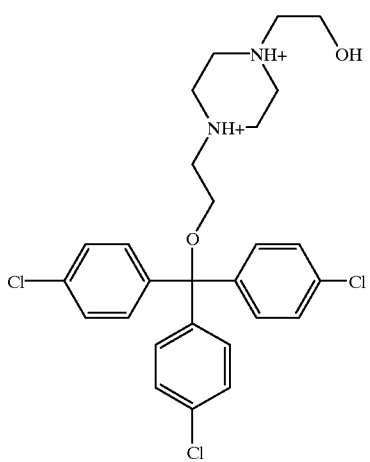
(7)
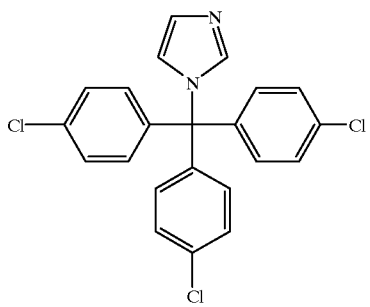
(8)
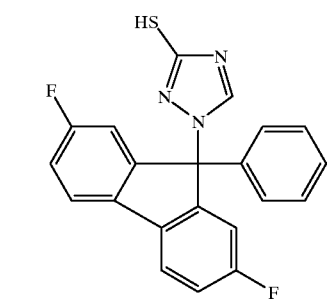

(9) 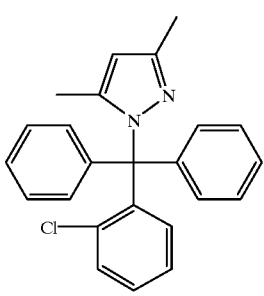
(10) 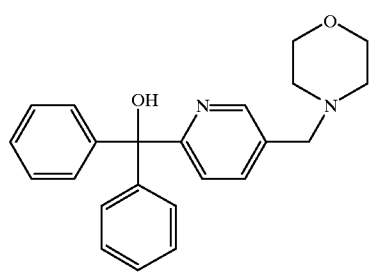
(11) 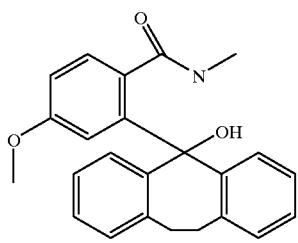
(12) 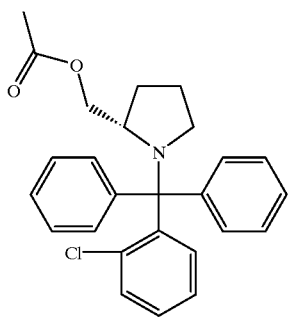
(13) 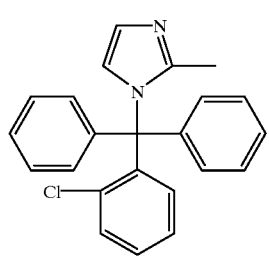
(14) 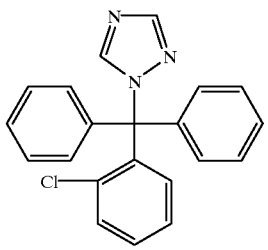
(15) 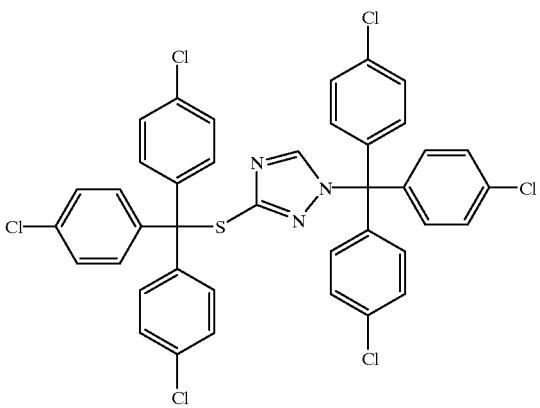
(16) 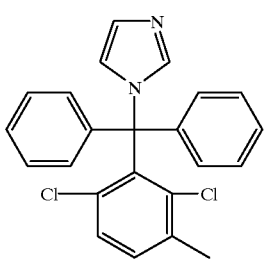
(17) 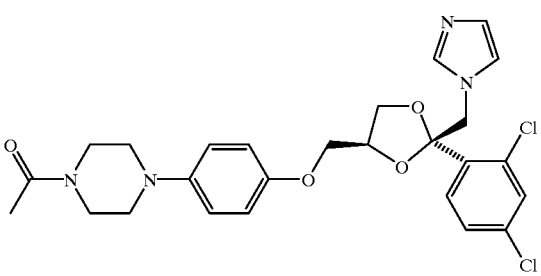
Names of Compounds:
1 Clotrimazole
2 N-(Triphenylmethyl)imidazole
3 N-([2-Fluoro-9-phenyl]fluorenyl)imidazole
4 N-([2-Pyridyl]diphenylmethyl)imidazole
5 N-(2-[4,4',4"-Trichlorotrityl]oxyethyl)morpholine
6 1-(2[4,4',4"-Trichlorotrityl]oxyethyl)-4-(2-hydroxyethyl) piperazine dimaleate
7 N-([4,4',4"]-Trichlorotrityl)imidazole 8   9-(3-Mercapto-1,2,4-trazolyl)-9-phenyl-2,7-difluorofluorenone
9   1-(2-Chlorotrityl)-3,5-dimethylpyrazole
10  4-(Morpholinomethyl)-A-(2-pyridyl)benzhydrol
11  5-(5-Methoxy-2-(N-methylcarbamoyl)phenyl) dibenzosuberol
12  N-(2-Chlorotrityl)-L-prolinol acetate
13  1-(2-Chlorotrityl)-2-methylimidazole
14  1-(2-Chlorotrityl)-1,2,4-triazole
15  1, S-Bis(4,4',4"-trichlorotrityl)-1,2,4-triazole-3-thiol
16  N-((2,6-dichloro-3-methylphenyl)diphenyl)methylimidazole
17  Ketoconazole Topical formulations contain about 0.05 to 5 wt. % of a non-steroidal glucocorticoid antagonist. Systemic formulations contain about 10 to 1000 mg.

The formulations can be administered systemically or topically, preferably topically, one to four times daily according to the discretion of a skilled clinician.

The following examples are not meant to be limiting.

EXAMPLE 1

N-(Triphenylmethyl)imidazole (2)

A stirred suspension of triphenylmethanol (2.6 g, 10 mmol) and 1.36 g (20 mmol) of imidazole in 10 mL of HOAc was heated to 100° C. under $N_2$ for 1 h. The cooled mixture was diluted with $Et_2O$ and washed with water, saturated $Na_2CO_3$, water (until neutral), brine, dried ($MgSO_4$), filtered and concentrated. The crude product was purified by flash chromatography (110 g $SiO_2$, 25%–50% EtOAc-hexanes) to give 0.78 g (25%) of a solid. This was recrystallized from EtOAc to give 0.20 g of (2), m.p. 221°–223° C.

IR (KBr) 1489, 1443, 1210, 1072, 750, 701, 662 $cm^{-1}$.

NMR ($CDCl_3$): δ6.82, 7.07, 7.47 (all t, J=1, imidazole CH); 7.14 (m, 6H); 7.32 (m, 9H).

| Anal. Calc'd ($C_{22}H_{18}N_2$): | C, 85.13; | H, 5.84; | N, 9.03. |
|---|---|---|---|
| Found: | 85.16; | 5.87; | 9.02. |

EXAMPLE 2

N-([2-Fluoro-9-phenyl]fluorenyl)imidazole (3)

a. To a stirred, ice-cooled solution of 2-fluorofluorenone (2.0 g, 10 mmol) in 15 mL of dry THF under $N_2$ was added 10 mL of 2.4 M phenyllithium solution in cyclohexane-$Et_2O$ (7:3), keeping T<20° C. The mixture was quenched with water and the product isolated with EtOAc and purified by flash chromatography (7% EtOAc-hexanes) to give 2.52 g (90%) of 2-fluoro-9-phenylfluoren-9-ol.

b. A solution of the above alcohol (0.57 g, 2.1 mmol) and imidazole (0.56 g, 8.4 mmol) in 6 mL of HOAc was heated to reflux under $N_2$ for 9.5 h. The crude product was isolated as described for (2) and purified by flash chromatography (30 g $SiO_2$, 50% EtOAc-hexanes) giving 0.40 g (59%) of a foam. This material was recrystallized from EtOAc to give 0.19 g of (3), m.p. 191.5°–194° C.

IR (KBr)1594, 1493, 1468, 1455, 1274, 1259, 1226, 1074, 862, 820, 766, 756, 744, 724, 702, 661 $cm^{-1}$.

NMR ($CDCl_3$): δ6.95 (s, 1H); 7.0–7.5 (m, 12H); 7.7 (m, 2H).

| Anal. Calc'd ($C_{22}H_{15}N_3F$): | C, 80.96; | H, 4.63; | N, 8.59. |
|---|---|---|---|
| Found: | 80.93; | 4.69; | 8.53. |

EXAMPLE 3

N-([2-Pyridyl]diphenylmethyl)imidazole (4)

A solution of diphenyl-2-pyridylmethanol (0.50 g, 1.9 mmol) and imidazole (0.50 g, 7.4 mmol) in 2 mL of $EtCO_2H$ was heated to reflux under $N_2$ for 7 h. The crude product was isolated as described for (2) and purified by flash chromatography (60 g $SiO_2$, EtOAc) to give 0.08 g (13.5%) of a yellow solid. This material was further purified by trituration (4:1 hexanes-$Et_2O$) followed by recrystallization from EtOAc to give 0.03 g of (4), m.p. 214.5°–216.5° C.

IR (KBr) 1584, 1487, 1462, 1444, 1430, 1212, 1066, 760, 710, 702, 666 $cm^{-1}$.

NMR ($CDCl_3$): δ7.05 (m, 7H); 7.3 (m, 7H); 7.65 (m, 2H); 8.70 (d, J=4, further split, 1H).

| Anal. Calc'd ($C_{21}H_{17}N_3$): | C, 81.00; | H, 5.50; | N, 13.50. |
|---|---|---|---|
| Found: | 81.17; | 5.50; | 13.69. |

EXAMPLE 4

N-([4,4',4"]-Trichlorotrityl)imidazole (7)

To a stirred solution of tris(4-chlorophenyl)methanol (0.36 g, 1.0 mmol) and imidazole (0.20 g, 2.9 mmol) in 2 mL of $CH_2Cl_2$ under $N_2$ at RT was added 0.40 mL (2.0 mmol) of trimethylsilyl triflate. After 1 h, the crude product was isolated as described for (2) and purified by flash chromatography (10% EtOAc-hexanes→EtOAc) to give 0.25 g of a semisolid. This material was triturated with 5% $Et_2O$-hexanes to give 0.20 g of (7) as a white solid, m.p. 153°–155° C.

IR (KBr) 1490, 1399, 1217, 1097, 1080, 1013, 815 $cm^{-1}$.

NMR ($CDCl_3$): δ6.77, 7.10, 7.41 (each s, 1H, imidazole CH); 7.04 (dt, 6H); 7.33 (dt, 6H).

| Anal. Calc'd ($C_{22}H_{15}N_2Cl_3$): | C, 63.86; | H, 3.65; | N, 6.77. |
|---|---|---|---|
| Found: | 63.96; | 3.95; | 6.70. |

EXAMPLE 5

9-(3-Mercapto-1,2,4-trazolyl)-9-phenyl-2,7-difluorofluorenone (8)

a. To a stirred, ice-cooled suspension of 2,7-difluorofluorenone (1.45 g, 6.7 mmol) in 50 mL of dry THF under $N_2$ was added 3.0 mL of 3.0 M ethereal phenylmagnesium bromide. The solution was diluted with $Et_2O$ and washed with water, 0.5 M $H_2SO_4$, water (until neutral), brine, dried ($MgSO_4$), filtered and concentrated to give 1.99 g (100%) of an oil. This material was triturated (5% $Et_2O$-hexanes) giving 1.11 g (56%) of 2,7-difluoro-9-phenylfluoren-9-ol.

b. To a stirred solution of the above alcohol (1.10 g, 3.74 mmol) and 1,2,4-triazole-3-thiol (0.56 g, 5.5 mmol) in 4.5 mL of dry $CH_2Cl_2$ under $N_2$ was added 1.25 mL (10 mmol) of $BF_3$ etherate. After 20 min, the mixture was poured into saturated aqueous $KH_2PO_4$ and the crude product was isolated with EtOAc and purified by flash chromatography (100 g $SiO_2$, 10%→50% EtOAc-hexanes) giving 0.41 g of a solid. This material was recrystallized from MeOH to give 0.25 g of (8), m.p. 209°–211° C. (dec).
IR (KBr) 1614 (w), 1595, 1466, 1436, 1259, 1210, 816, 740 $cm^{-1}$.
NMR (DMSO-$d_6$): δ7.2 (m, 7H); 7.5 (m, 2H); 7.83 (q, 2H); 8.28 (s, 1H, triazole CH); 14.0 (br s, 1H, SH).

| Anal. Calc'd ($C_{21}H_{13}N_3F_2S$): | C, 66.83; | H, 3.47; | N, 11.13. |
|---|---|---|---|
| Found: | 66.79; | 3.84; | 11.23. |

EXAMPLE 6

1, S-Bis(4,4',4''-trichlorotrityl)-1,2,4-triazole-3-thiol (15)

The procedure of Example 5(b) was followed, using 1.26 g (3.47 mmol) of tris(4-chlorophenyl)methanol, 0.52 g (5.1 mmol) of 1,2,4-triazole-3-thiol, 4.0 mL of $CH_2Cl_2$ and 1.25 mL (10 mmol) of $BF_3$ etherate. Isolation followed by flash chromatography (75 g $SiO_2$, 40% EtOAc-hexanes) gave 0.51 g of the title compound, followed by 0.71 g of an unstable product that turned into the title compound upon standing in solution. A 0.44 g sample of the first-eluted material was recrystallized from MeOH giving 0.18 g of (15), m.p. 219°–221° C. (dec).
IR (KBr) 1490, 1399, 1257, 1097, 1013, 815 $cm^{-1}$.
NMR ($CDCl_3$): δ6.75 (d, J=9, 6H); 7.05–7.3 (m, 18H); 7.59 (s, 1H).

| Anal. Calc'd ($C_{40}H_{25}Cl_6N_3S$): | C, 60.62; | H, 3.18; | N, 5.30. |
|---|---|---|---|
| Found: | 60.72; | 3.41; | 5.23. |

EXAMPLE 7

1-(2-Chlorotrityl)-3,5-dimethylpyrazole (9)

a. To a stirred, ice-cooled solution of 2-chlorobenzophenone (21.6 g, 100 mmol) in 150 mL of dry $Et_2O$ under $N_2$ was added 60 mL (120 mmol) of 2.0 M phenyllithium solution in cyclohexane-$Et_2O$ (7:3), keeping T<15° C. After stirring for a further 1 h at 15° C., the solution was poured onto crushed ice and extracted with $Et_2O$. The organic solution was washed with 0.2 M $H_2SO_4$, water (until neutral), brine, dried ($MgSO_4$), filtered and concentrated. The residue was recrystallized from hexanes containing a few per cent EtOAc to give 23.1 g (78%) of (2-chlorophenyl)diphenylmethanol as an off-white solid.
NMR ($CDCl_3$): δ4.43 (s, 1H, OH); 6.70 (dd, J=7.8 and 1.7, 1H); 7.11 (dt, J=7.8 and 1.5, 1H); 7.2–7.45 (m, 12H).
b. The above alcohol (4.20 g, 14.3 mmol) was dissolved in $SOCl_2$ (5.0 mL, 68 mmol) under $N_2$. The nitrogen line was replaced with a $CaSO_4$ drying tube. After a 1-min induction period, gas was rapidly evolved (CAUTION!). A further 3.4 mL (47 mmol) of $SOCl_2$ was added, followed by 4 mL of toluene. Stirring was continued for 6 h. The solution was then concentrated under reduced pressure, the residue dissolved in toluene, concentrated and vacuum pumped to give 4.40 g (99%) of (2-chlorophenyl)diphenylchloromethane as a solid.
NMR ($CDCl_3$): δ6.80 (dd, J=7.7 and 1.7, 1H); 7.10 (dt, J=7.3 and 1.5, 1H); 7.2–7.45 (m, 12H). This material contained 10% of the starting alcohol by NMR.
c. A solution of the above chloride (0.63 g, 2.0 mmol), 3,5-dimethylpyrazole (0.38 g, 4.0 mmol) and ethyldiisopropylamine (0.70 mL, 4.0 mmol) in dry DMF was stirred under $N_2$ for 16 h, then heated to 50° C. for 2 h. The mixture was poured into saturated $Na_2CO_3$ and the crude product isolated by EtOAc extraction and purified by flash chromatography (125 g $SiO_2$, 10% EtOAc-hexanes, then 50 g $SiO_2$, 5% EtOAc-hexanes) giving 0.18 g of a solid. This material was triturated with $Et_2O$, then recrystallized from EtOAc-MeOH to give 0.09 g of (9), m.p. 195°–197° C.
IR (KBr) 1557, 1493, 1445, 1434, 1349, 1044, 906, 764, 746, 704, 696 $cm^{-1}$.
NMR ($CDCl_3$): δ1.40, 2.20 (each s, 3H); 5.90 (s, 1H, pyrazole CH); 7.0–7.5 (m, 14H).

| Anal. Calc'd ($C_{24}H_{21}N_2Cl$): | C, 77.30; | H, 5.68; | N, 7.51. |
|---|---|---|---|
| Found: | 77.42; | 5.86; | 7.46. |

EXAMPLE 8

1-(2-Chlorotrityl)-2-methylimidazole (13)

A solution of the chloride of Example 7(b) (0.93 g, 3.0 mmol), 2-methylimidazole (0.50 g, 6.1 mmol) and ethyldiisopropylamine (1.1 mL, 6.3 mmol) in 5 mL of dry DMF was stirred at RT under $N_2$ for 2.5 h. The crude product was isolated by EtOAc extraction and purified by flash chromatography (100 g $SiO_2$, 70% EtOAc-hexanes) followed by spontaneous crystallization from EtOAc to give 0.6 g of (13), m.p. 177° C.
IR (KBr) 1492, 1444, 1432, 1397, 1238, 766, 753, 710 $cm^{-1}$.
NMR ($CDCl_3$): δ1.57 (s, 3H); 6.82 (d, 2H); 7.0–7.5 (m, 14H).

| Anal. Calc'd ($C_{23}H_{19}N_2Cl$): | C, 76.97; | H, 5.34; | N, 7.81. |
|---|---|---|---|
| Found: | 76.95; | 5.49; | 7.67. |

EXAMPLE 9

1-(2-Chlorotrityl)-1,2,4-triazole (14)

The procedure described for (13) was followed, substituting 1,2,4-triazole (0.42 g, 6.1 mmol) for 2-methylimidazole. The crude product was recrystallized from acetone giving 0.6 g of (14), m.p. 160° C.
IR (KBr) 1497, 1446, 1434, 1277, 1142, 768, 751, 697 $cm^{-1}$.
NMR ($CDCl_3$): δ6.9 (d, 1H); 7.0–7.5 (m); 8.06 and 8.18 (each s, 1H).

| Anal. Calc'd ($C_{21}H_{16}N_3Cl$): | C, 72.93; | H, 4.66; | N, 12.15. |
|---|---|---|---|
| Found: | 72.95; | 4.70; | 12.07. |

EXAMPLE 10

N-(2-Chlorotrityl)-L-prolinol acetate (12)

The procedure described for (13) was followed, using 1.47 g (4.7 mmol) of the chloride of Example 7(b), 0.55 g (5.5 mmol) of L-prolinol, 1.1 mL (6.3 mmol) of ethyldiisopropylamine and 10 mL of dry DMF. After 24 h, the crude product was isolated with EtOAc and purified by flash chromatography giving 0.84 g of a foam (major rotamer). A 0.30 g (0.79 mmol) sample of this material was acetylated (2 mL Ac$_2$O, 4 mL pyridine, RT, 16 h), the product was isolated (EtOAc) and recrystallized (MeOH) giving 0.24 g of (12), m.p. 102°–104° C.

IR (KBr) 1736, 1444, 1240, 1040, 756, 707 cm$^{-1}$.

NMR (CDCl$_3$): δ0.43 (m, 1H); 1.1–1.5 (3H); 2.00 (s, 3H); 2.8, 3.1 (AB, 2H, CH$_2$N); 3.5 (m, 1H, CHN); 3.9 (t, J=9,1H) and 4.05 (dd, 1 H); 7.0–7.5 (m, 11H); 7.7 (dd, J=8, 1.2, 2H); 8.35 (d, J=8, 1H).

| Anal. Calc'd (C$_{26}$H$_{26}$ClO$_2$N): | C, 74.36; | H, 6.24; | N, 3.34. |
|---|---|---|---|
| Found: | 74.17; | 6.31; | 3.31. |

EXAMPLE 11

N-(2-[4,4',4"-Trichlorotrityl]oxyethyl)morpholine (5)

a. Dry DMSO (20 mL) was added to 14 mmol of hexane-washed KH under Ar with stirring at RT. After H$_2$ evolution ceased, a solution of tris-(p-chlorophenyl)methanol (3.63 g, 10 mmol) in 25 mL dry DMSO was added, giving a deep red anion solution. After 5 min,1-bromo-3-methyl-2-butene (2.0 mL, 19 mmol) was added and stirring continued for 1 h. The crude product was isolated by Et$_2$O extraction and purified by flash chromatography (75 g SiO$_2$, 5% EtOAc-hexanes) giving 3.93 g (91%) of (3-methyl-2-butenyl) tris-(4-chlorophenyl) methyl ether as an oil.

NMR (CDCl$_3$): δ1.47, 1.72 (each s, 3H); 3.54 (d, 2H); 5.4 (t, 1H), 7.1–7.4 (m, 12H).

b. m-Chloroperoxybenzoic acid (80%, 2.15 g, 10 mmol) was added to a stirred suspension of 3.06 g (7.1 mmol) of the above allylic ether and 0.84 g (10 mmol) of NaHCO$_3$ in 50 mL of CH$_2$Cl$_2$. After 17 h, the mixture was diluted with EtOAc, washed with saturated Na$_2$CO$_3$, water (until neutral), brine, dried (MgSO$_4$) filtered and concentrated. The crude product was purified by flash chromatography (100 g SiO$_2$, 10% EtOAc-hexanes) giving 2.90 g (91%) of the epoxy ether as a white solid.

NMR (CDCl$_3$): δ1.13, 1.33 (each s, 3H); 3.03 (m, 1H, epoxy); 3.2 (m, 2H); 7.2–7.4 (m, 12H).

c. Periodic acid (1.90 g, 8.33 mmol) was added to a stirred solution of the above epoxy ether (2.87 g, 6.4 mmol) in 60 mL of dry Et$_2$O and 15 mL of CH$_2$Cl$_2$. After 1 h, the solution was washed with saturated NaHCO$_3$, water (until neutral), brine, dried (MgSO$_4$), filtered and concentrated giving 2.63 g of crude aldehyde as a foam. This material was dissolved at once in 60 mL of MeCN.

d. Morpholine (0.23 mL, 2.6 mmol) was added to a 12 mL portion of the above aldehyde/MeCN solution, followed by NaBH$_3$CN (0.25 g, 4.0 mmol). After 30 min the reaction was quenched with HOAc (2 mL), allowed to stand for 15 min, and poured into saturated Na$_2$CO$_3$. The crude product was isolated by EtOAc extraction and purified by flash chromatography (70 g SiO$_2$, 40% EtOAc-hexanes) giving 0.32 g of a solid. This material was recrystallized from EtOH, giving 0.21 g of (5), m.p. 151°–153° C.

IR (KBr) 1490, 1117, 1093, 1066, 1014, 817 cm$^{-1}$.

NMR (CDCl$_3$): δ2.46 (br t, J=4.6, 4H); 2.62 (t, J=6, 2H); 3.14 (t, J=6, 2H); 3.70 (br t, J=4.6, 4H); 7.3 (m, 12H).

| Anal. Calc'd: | C, 62.97; | H, 5.07; | N, 2.94. |
|---|---|---|---|
| Found: | 62.93; | 5.06; | 2.91. |

EXAMPLE 12

1-(2[4,4',4"-Trichlorotrityl]oxyethyl)-4-(2-hydroxyethyl)piperazine dimaleate (6)

N-(2-hydroxyethyl)piperazine (0.32 mL, 2.6 mmol) was added to a 12 mL portion of the aldehyde/MeCN solution of Example 11(c). The mixture was quenched and extracted as above, and the crude free base dissolved in EtOH and treated with maleic acid (0.085 g, 0.73 mmol). The resulting solution was concentrated and triturated with Et$_2$O giving a white solid, which was recrystallized (EtOH-EtOAc) to give 0.05 g of (6), m.p. 173°–176° C. (dec).

IR (KBr) 3409 (br), 1702 (w), 1616 (m), 1578, 1488, 1356, 1094, 920 cm$^{-1}$.

| Anal. Calc'd (C$_{27}$H$_{29}$N$_2$O$_2$Cl$_3$ [C$_4$H$_4$O$_4$]$_2$): | C, 55.89; | H, 4.96; | N, 3.73. |
|---|---|---|---|
| Found: | 55.72; | 5.17; | 3.73. |

EXAMPLE 13

N-((2.6-Dichloro-3-methylphenyl)diphenyl)methylimidazole (16)

A solution of (2,6-dichloro-3-methylphenyl)diphenylmethanol (0.40 g, 1.2 mmol) and imidazole (0.50 g, 7.4 mmol) in 2 mL of acetic acid was heated to reflux for 2 h and then allowed to stand at RT for two days. The product was isolated by EtOAc/H$_2$O partition followed by chromatography (75 g SiO$_2$, 50% EtOAc-hexane) to give 0.40 g (87%) of (16) as a white foam.

NMR (CDCl$_3$): δ2.36 (s, 3H); 6.56 (s, 1H); 7.3 (m, 12H); 7.83 (s, 1H).

EXAMPLE 14

Topical Ocular Formulation of Non-steroidal Glucocorticoid Antagonist

| Ingredient | Amount (wt. %) |
|---|---|
| Clotrimazole | 1.00 |
| Mannitol | 2.40 |
| Sodium Chloride | 0.40 |
| Carbopol 974P | 0.50 |
| Polysorbate 80 | 0.05 |
| Edetate Sodium | 0.01 |
| Benzalkonium Chloride | 0.01 |
| Sodium Hydroxide | Adjust pH to 7.2 |
| Purified Water | qs to 100% |

EXAMPLE 15

Formulation for Oral Administration

Tablet: 10–1000 mg of non-steroidal glucocorticoid antagonist with inactive ingredients such as cornstarch, lactose, colloidal silicon dioxide, microcrystalline cellulose, and magnesium stearate can be formulated according to procedures known to those skilled in the art of tablet formulation.

We claim:
1. A compound selected from the group consisting of:
N-(2-[4,4',4''-Trichlorotrityl]oxyethyl)morpholine;
1-(2[4,4',4''-Trichlorotrityl]oxyethyl)-4-(2-hydroxyethyl) piperazine dimaleate;
9-(3-Mercapto-1,2,4-trazolyl)-9-phenyl-2,7-difluorofluorenone;
1-(2-Chlorotrityl)-3,5-dimethylpyrazole;
N-(2-Chlorotrityl)-L-prolinol acetate;
1, S-Bis(4,4',4''-trichlorotrityl)-1,2,4-triazole-3-thiol.

2. A method for treating glaucoma or ocular hypertension by administering a pharmaceutically effective amount of a compound of claim 1 in a pharmaceutically acceptable carrier.

3. A composition for controlling glaucoma or ocular hypertension comprising a pharmaceutically effective amount a compound of claim 1.

* * * * *